United States Patent [19]
Ishii et al.

[11] Patent Number: 5,498,627
[45] Date of Patent: Mar. 12, 1996

[54] OCTAHYDRO-2-NAPHTHALENECARBOXYLIC ACID DERIVATIVE, ITS PRODUCTION AND USE

[75] Inventors: Takafumi Ishii, Ibaraki; Tsuneaki Hida, Tsukuba; Yukimasa Nozaki, Ikeda; Koichiro Ootsu, Mishima, all of Japan

[73] Assignee: Takeda Chemical Industries, Ltd., Osaka, Japan

[21] Appl. No.: 421,921

[22] Filed: Apr. 14, 1995

[30]  Foreign Application Priority Data

Apr. 15, 1994 [JP] Japan .................................. 6-077225
Nov. 29, 1994 [JP] Japan .................................. 6-295048

[51] Int. Cl.⁶ ........................ A61K 31/40; C07D 207/24
[52] U.S. Cl. ......................... 514/423; 548/539; 435/121; 435/254.1
[58] Field of Search ........................... 514/423; 548/539

[56] References Cited

FOREIGN PATENT DOCUMENTS

| | | |
|---|---|---|
| 4-74163 | 3/1992 | Japan . |
| 4-316578 | 11/1992 | Japan . |
| 6-277084 | 10/1994 | Japan . |
| WO-A-9324643 | 9/1993 | WIPO . |
| WO94-00430 | 1/1994 | WIPO . |

OTHER PUBLICATIONS

James, et al., "Benzodiazepine Peptidomimetics: Potent Inhibitors of Ras Farnesylation in Animal Cells", Science, vol. 260, 25, Jun. 1993 pp. 1937–1942.
Chemical Abstracts, vol. 121, No. 13, 1994, Columbus, Ohio, US; Abstract No. 157425g, (Ishizuka et al).
Chemical Abstracts, vol. 122, No. 5, 1995, Columbus, Ohio, US; Abstract No. 54155k, (Tamamura et al).
Bos: "ras Oncogenes in Human Cancer: A Review"; Cancer Research 49, pp. 4682–4689, (Sep. 1, 1989).
Willumsen et al, "The p21 ras C–terminus is required for transformation and membrane association"; Nature vol. 310 16 (Aug. 1984), pp. 583–586.
Gibbs, et al, "Zenopus oocyte germinal–vesicle breakdown induced by [Val$^{12}$] Ras is inhibited by a cytosol–localized Ras mutant"; Proc. Natl. Acad. Sci. USA, vol. 86, pp. 6630–6634, (Sep. 1989).
Clarke, "Protein isoprenylation and methylation at carboxyl–terminal cysteine residues", Annu. Rev. Biochem. (1992) 61 pp. 355–386.
Schafer, et al, "Protein prenylation: genes, enzymes, targets, and functions", Annu. Rev. Genet. (1992), 30 pp. 209–237.
Reiss, et al, "Inhibition of purified p21$^{ras}$ farnesyl:protein transferase by cys–AAX tetrapeptides"; Cell, vol. 62, pp. 81–88, Jul. 13, 1990.
Tamanoi, "Inhibitors of ras farneslyltransferases", TIBS 18, (Sep. 1993), pp. 349–353.
Miura, et al, "Inhibition of protein prenylation by patulin", FEBS 12137, vol. 318, No. 1, pp. 88–90, (Feb. 1993).
Kohl et al, "selective inhibition of ras–dependent transformation by a farnesyltransferase inhibitor", Science, vol. 260, (25 Jun. 1993) pp. 1934–1937.
Kothapalli et al, "Farnesylamine: an inhibitor of farnesylation and growth of 35 U.S.C. ras–transformed cells", Lipids, vol. 28, No. 11 (1993), pp. 969–973.
Mosmann, "Rapid colorimetric assay for cellular growth and survival: application to proliferation and cytotoxicity assays", Journal of Immunological Methods, 65, (1983) pp. 55–63.
Ueno et al., "Delaminomycins, Novel Nonpeptide Extracellular Matrix Receptor Antagonist and A New Class of Potent Immunomodulator", Journal of Antibiotics, vol. 46, No. 6, pp. 979–984, Jun. 1993.

*Primary Examiner*—Joseph Paul Brust
*Attorney, Agent, or Firm*—Wenderoth, Lind & Ponack

[57] ABSTRACT

This invention provides a novel compound TAN-1813 having farnesyltransferase-inhibitory, cell growth-inhibitory, and anti-tumor activities; its production; farnesyltransferase-inhibiting agent; anti-tumor agent; pharmaceutical composition comprising a compound TAN-1813; and a novel microorganism capable of producing said compound.

4 Claims, 4 Drawing Sheets

OCTAHYDRO-2-NAPHTHALENECARBOXYLIC ACID DERIVATIVE, ITS PRODUCTION AND USE

BACKGROUND OF THE INVENTION

1. Field of the Invention

The present invention relates to a novel octahydro-2-naphthalenecarboxylic acid derivative (hereinafter designated as compound TAN-1813) useful as a farnesyltransferase inhibitor, and its production and use.

2. Description of Related Art

Ras gene is widely conserved in eukaryotic cells. Recent studies have revealed that ras gene product (ras protein) plays important roles as a signal transducer in regulating cell growth and differentiation. Further, point mutation of ras gene is frequently observed in various tumors. It is well established that mutated ras Proteins are always fixed in a GTP-bound activated form, and thereby the growth-promoting signal is always transduced (Cancer Research 49, 4682 (1989)). The ras protein is a GTP-binding protein having a molecular weight of about 21,000. Farnesylisoprenoid is attached to the C-terminal cysteine residue of the protein by three steps of post-translational modifications. It is believed that the growth-promoting signal is transferred only when the protein is localized in cell plasma membrane using the farnesylisoprenoid as an anchor (Nature 310, 583 (1984), Proceedings of the National Academy of Science, USA 86, 6630 (1989), etc.). Therefore, it is expected that inhibition of ras protein farnesylation blocks function of the ras protein, and thereby inhibits growth of the tumor harboring ras mutation.

On the other hand, a unique amino acid sequence motif is observed in the C-terminal region of ras protein. The amino acid sequence motif is represented by CAAX wherein C is cysteine, A is an aliphatic amino acid and X is usually serine or methionine (Annual Review of Biochemistry) 61, 355 (1992), Annual Review of Genetics 30, 209 (1992), etc.). Farnesyltransferase was isolated from rat brains as an enzyme that recognizes the CAAX motif of ras protein to transfer farnesylpyrophosphate, a cholesterol biosynthetic intermediate, to the cysteine residue (Cell 62, 81 (1990)).

Examples of microbial substances having farnesyltransferase-inhibitory activity are 10'-desmethoxystreptonigrin, gliotoxins, pepticinnamins, manumycins, zaragozic acids, chaetomellic acids (Trends in Biochemical Sciences 18, 349 (1993)), patulin (FEBS Letters 318, 88 (1993)), etc. Synthetic peptides that are analogues of the tetrapeptide CAAX (Science 260, 1934-1942 (1993), etc.), and synthetic analogues of another substrate, farnesylpyrophosphate (Lipid 28, 969 (1993), etc.) have also been reported as farnesyltransferase-inhibitory substances.

The farnesyltransferase-inhibitory substances described above have some disadvantages. For example, some of them have been proved to be metabolically unstable, to be impermeable to cells and/or have another biological activity other than farnesyltransferase inhibition and thus have poor specificity, leading to adverse side effects. Therefore, there is a need for novel farnesyltransferase inhibitors that are stable in vivo and have high specificity.

One object of the present invention is to provide a novel compound having farnesyltransferase-inhibitory, cell growth-inhibitory, and anti-tumor activities.

Another object of the present invention is to provide a farnesyltransferase-inhibiting agent.

Another object of the present invention is to provide an anti-tumor agent.

Another object of the present invention is to provide a microorganism capable of producing the novel compound.

These objects as well as other objects and advantages of the present invention will become apparent to those skilled in the art from the following description with reference to the accompanying drawings.

SUMMARY OF THE INVENTION

In order to solve the above problems, the present inventors have made intensive screening efforts to find a novel farnesyltransferase inhibitor in metabolites of microorganisms. As a result, they have succeeded in isolating a novel compound TAN-1813 from a culture broth, and found that this compound has farnesyltransferase-inhibitory, cell growth inhibitory, and anti-tumor activities. After further studies based on these findings, the present invention has been completed.

The present invention provides a compound TAN-1813 of the formula (I):

or a salt thereof.

The present invention also provides a farnesyltransferase-inhibiting agent comprising a compound TAN-1813 or a salt thereof.

The present invention also provides an anti-tumor agent comprising a compound TN-1813 or a salt thereof.

The present invention also provides a pharmaceutical composition comprising a compound TAN-1813 or a salt thereof and a pharmaceutically acceptable carrier.

The present invention also provides a method for producing a compound TAN-1813 or a salt thereof, which comprises cultivating a microorganism belonging to genus Phoma capable of producing the compound TAN-1813 in a medium to produce and accumulate the compound TAN-1813 in the culture, and then collecting the compound TAN-1813.

The present invention also provides Phoma sp. strain FL-41510 (FERM BP-4632) capable of producing a compound TAN-1813.

DETAILED DESCRIPTION OF THE INVENTION

Any microorganism can be used in the present invention as long as they belong to genus Phoma and are capable of producing the compound TAN-1813. Examples of the microorganisms include the filamentous fungus Phoma sp. strain FL-41510 isolated from a plant in Fukushima prefecture, Japan (FERM BP-4632). Strain FL-41510 has the following characteristics.

(a) Morphological characteristics

Aerial hyphae: The aerial hyphae have septa. The surface is smooth or rough. Each hypha is 1 to 1.5 μm in diameter. At places, many hyphae clump together in the form of a loop or rope.

Pycnidium: The pycnidium is buried and has a global to sub-global shape. It has one hole. It is dark brown. It is 150 to 200 μm in diameter.

Conidium: The conidium is a single cell. It is colorless. It has a smooth surface, and an oval to egg shape. It is 3–5×1.5–2 μm.

(b) Characteristics on agar media

The growth characteristics were observed after two week cultivation at 24° C.

1) Malt extract agar medium

The growth is moderate, and the spreading on the medium is slow. The diameter of the colony is 20 to 22 mm. The surface consists of protuberant wool-like mycelia. The outer edge is fringed somewhat irregularly. The surface is pale gray to gray white in the center to the edge. The reverse surface is dark gray black to dark gray in the center to the intermediate region, and pale gray in the edge region. No formation of a soluble pigment is observed.

2) Potato glucose agar medium

The growth is moderate, and the spreading on the medium is somewhat slow. The diameter of the colony is 33 to 35 mm. The surface consists of protuberant wool-like mycelia. The outer edge is fringed regularly. The surface is dark gray to pale gray in the center to the edge. The reverse surface is dark brown to pale brown in the center to the edge. Formation of a soluble pigment is observed.

3) Czapek agar medium

The growth is moderate. The diameter of the colony is 32 mm. The surface consists of somewhat protuberant wool-like mycelia. The outer edge is fringed regularly. The surface is dark black gray to pale black gray in the center to the intermediate region, and pale gray in the edge region. The reverse surface is dark black brown to pale black brown in the center to the edge. No formation of a soluble pigment is observed.

4) Oatmeal agar medium

The growth is moderate. The diameter of the colony is 42 mm. The surface consists of protuberant wool-like mycelia. The outer edge is fringed regularly. The surface is dark gray to pale gray in the center to the edge. The reverse surface is brown to pale brown in the center to the edge. No formation of a soluble pigment is observed.

(c) Physiological characteristics

The conditions for the growth of the strain were determined on potato glucose agar medium. It grew at pH range of 3 to 12. The temperature for the growth was 6° to 32° C. The optimum temperature for the growth was 25° to 29° C.

Based on the above characteristics, by reference to the table at page 51 of "Separation, Cultivation and Characterization of Mold (Kabi No Bunri, Baiyo To Dotei)" written by D. Malloch and translated by Shun-ichi Udagawa, 1983, Ishiyaku Shuppan Kabushiki Kaisha, it is clear that this strain belongs to the genus Phoma because the spore consists of a single cell, the colony, conidium and other apparatuses have dark color, the conidium is not linked and forms in the pycnidium, and the hyphae have septa. This strain then was identified as Phoma sp. FL-41510.

This strain has been deposited at Institute for Fermentation, Osaka (IFO), Japan under the accession number IFO 32613 since Mar. 1, 1994. It has also been deposited at National Institute of Bioscience and Human-Technology (NIBH), Agency of Industrial Science and Technology, Japan, 1–3, Higashi 1 chome Tsukuba-shi Ibaraki-ken 305, Japan under the Budapest Treaty under the accession number FERM BP-4632 since Apr. 11, 1994.

The compound TAN-1813 or a salt thereof of the present invention can be produced by cultivating in a medium a microorganism capable of producing the compound, such as the above strain or variants derived from this strain by per se known methods (e.g., genetic manipulation techniques, irradiation with radiations such as X-ray, gamma ray, ultraviolet light, etc., treatment with drugs, cultivation on a chemical-containing medium, etc.), to produce and accumulate the compound in the culture, and then collecting the compound.

The medium used for the cultivation of the microorganism producing the compound of the present invention may be liquid or solid as long as it contains nutritional sources that the microorganism can use. Liquid media are suitably used for large-scale production. Carbon sources, nitrogen sources, inorganic substances, and traces of nutritional sources that the microorganism can assimilate are appropriately added to the medium. Examples of the carbon sources include glucose, lactose, sucrose, maltose, dextrin, starch, glycerin, mannitol, sorbitol, oils and fats (e.g., soybean oil, lard oil, chicken oil, etc.), n-paraffin, etc. Examples of the nitrogen sources include meat extract, yeast extract, dried yeast, soybean flour, corn steep liquor, peptone, cotton seed flour, waste syrup, urea, and ammonium salts (e.g., ammonium sulfate, ammonium chloride, ammonium nitrate, ammonium acetate, etc.). Further, there can appropriately be used salts including sodium, potassium, calcium, magnesium, etc.; metal salts such as iron, manganese, zinc, cobalt, nickel, etc.; salts such as phosphate, borate, etc.; salts of organic acids such as acetic acid, propionic acid, etc.; etc. In addition, the medium may contain amino acids (e.g., glutamic acid, aspartic acid, alanine, lysine, methionine, proline, etc.), peptides (e.g., dipeptides, tripeptides, etc.), vitamins (e.g., vitamin $B_1$, vitamin $B_2$, nicotinic acid, vitamin $B_{12}$, vitamin C, etc.), nucleic acids (e.g., purine, pyrimidine, derivatives thereof, etc.), etc. Inorganic or organic acids or alkalis, buffers, etc., can be added to control the pH of the medium. Suitable amounts of oils and fats, surfactants, etc., can be added to prevent foaming. In the case of liquid culture, the pH of the medium is about a neutral pH, preferably pH 6 to 8. The cultivation temperature is preferably about 20° to 30° C., and the cultivation time is preferably about 48 to 168 hours. The cultivation is carried out according to per se known methods such as stationary culture, shaking culture, or aerobic and agitating culture, etc. Aerobic and agitating culture is preferred for large-scale production. Normally, the maximum production of the compound TAN-1813 can be achieved by cultivation for 4 to 6 days.

The compound TAN-1813 can be collected from the culture broth as follows. Because the compound is fatsoluble in acidic conditions, conventional means using this property can be used.

In the culture broth, the compound (I) is contained in the cells and culture supernatant. First, the culture broth is therefore adjusted to pH 2 to 7, preferably pH 2.5 to 4.0, then an organic solvent immiscible with water (e.g., chloroform, ethyl acetate, methyl isobutyl ketone, butanol, etc.) is added. The mixture is stirred for about 10 minutes to 20 hours, preferably about 20 minutes to 4 hours, and is filtered after adding a filter aid, or centrifuged to separate the organic layer. The organic layer thus obtained is washed with water and concentrated to give crude material containing the compound TAN-1813. Alternatively, the organic layer is extracted with an aqueous solution of an appropriate basic salt such as sodium bicarbonate, sodium carbonate, etc., to transfer the compound TAN-1813 to aqueous solution from the organic layer. Then, the aqueous layer is adjusted to pH 2 to 7, preferably pH 2.5 to 4, and extracted again with the above organic solvent immiscible with water. The extract is then concentrated to give crude material containing the compound TAN-1813.

Various chromatography techniques can be advantageously used to further purify the crude material and obtain the pure compound TAN-1813. Examples of supports include silica gel, crystalline cellulose, Sephadex LH-20 (manufactured by Pharmacia, Sweden), adsorptive resins, anion-exchange resins, etc. Normally, column chromatography is used. To elute the active compound from the support, an appropriate organic solvent such as hexane, chloroform, toluene, ethyl acetate, dichloromethane, acetone, acetonitrile, methanol, acetic acid, formic acid, etc., alone or a mixture thereof can be used. A mixture of the solvent with water can also be used.

High performance liquid chromatography (HPLC) can also be used to purify the compound TAN-1813. Preferred examples of supports include octadecyl silane (ODS) type supports and silica gel type supports. When an ODS type support is used, the eluent is preferably a mixed solution of methanol or acetonitrile with a salt-containing aqueous solution. Concentration of the eluate gives crude powder. Alternatively, when the eluate is an aqueous solution, the eluate is extracted with an appropriate organic solvent immiscible with water, and concentrated to give crude powder. The crude powder is dissolved in an appropriate solvent such as petroleum benzine, petroleum ether, hexane, toluene, ether, chloroform, ethyl acetate, acetonitrile, ethanol, methanol, or a mixture thereof. The solution is allowed to stand in a cold place to give purified powder of the compound TAN-1813.

The compound of the present invention can also be obtained as a physiologically acceptable salt with an alkaline metal (e.g., sodium, potassium, etc.), alkaline earth metal (e.g., calcium, magnesium, etc.), inorganic base (e.g., ammonia, etc.), organic amine (e.g., methylamine, ethylamine, propylamine, isopropylamine, butylamine, tert-butylamine, dimethylamine, diethylamine, trimethylamine, triethylamine, pyridine, picoline, dicyclohexylamine, N,N'-dibenzylethylenediamine, etc.), organic base such as amino acids (e.g., lysine, arginine, etc.), etc., by per se known methods.

The following Experiments illustrate biological activity of the compound TAN-1813.

Experiment 1

Farnesyltransferase-inhibitory test
Method:

Farnesyltransferase was prepared from rat brains according to the method of Y. Reiss et al. (Cell 62, 81 (1990)) and all of the following procedures were performed at 4° C. That is, brains were removed from SD rats (male, 6 weeks old, Charles River) and sliced with a pair of scissors. Then 50 mM tris-hydrochloric acid buffer (pH 7.5)(2 ml per brain) containing 1 mM EDTA, 1 mM EGTA, 0.2 mM phenylmethylsulfonyl fluoride and 0.1 mM leupeptin was added. The mixture was homogenized with a Teflon homogenizer (manufactured by Hamada Rika, Japan) in ice. The extract was centrifuged at 60,000×g for 70 minutes. From the resulting supernatant, the precipitate fraction from 30 to 50 W/V % concentration of ammonium sulfate was recovered, and dialyzed overnight against 20 mM tris-hydrochloric acid buffer (pH 7.5) containing 1 mM dithiothreitol and 20 µM zinc chloride. The dialysed solution was centrifuged at 15,000×g for 10 minutes. The resulting supernatant was used as a crude enzyme solution.

Farnesyltransferase activity was determined using FT Assay Kit (manufactured by Amersham) as follows. A mixture of 20 µl of the compound TAN-1813 and 20 µl of the above crude enzyme solution was added to a reaction mixture (60 µl) containing a peptide (100 nM) modified with biotin, said peptide consisting of 11 amino acid residues of the C-terminal of human lamin B; 120 nM $^3$H-farnesylpyrophosphate; 6 mM magnesium chloride; 4 mM potassium chloride; 1 mM dithiothreitol; 0.002% Triton X-100; and 10 mM HEPES buffer (pH 7.5). The mixture was incubated at 37° C. for 1 hour, and then the reaction was stopped by addition of SPA beads solution (manufactured by Amersham) (150 µl). The radioactivity produced by attachment of the $^3$H-farnesylated peptide to the SPA beads was measured with a scintillation counter to determine the amount of the $^3$H-farnesylated peptide. The farnesyltransferase-inhibitory activity of the compound TAN-1813 was calculated from the counts in the presence and absence of the compound TAN-1813.

Results:

The compound TAN-1813 inhibited farnesyltransferase activity by 50% at 12 µg/ml.

Experiment 2

Cell growth-inhibitory test
Method:

The cell growth-inhibitory activity of the compound TAN-1813 was determined according to a modified method of Mosmann (Journal of Immunological Methods 65, 55 (1983) ) by using a K-ras transformant (NIH3T3/K-ras) of mouse embryonic fibroblast strain NIH3T3. That is, NIH3T3/K-ras cells were suspended in a medium at a cell density of $3\times10^4$/ml. The suspension (0.1 ml per well) was dispensed into each well of a 96-well flat-bottomed plate (manufactured by Nunc) containing a solution (10 µl) of varying concentrations of the compound TAN-1813 dissolved in phosphate-buffered saline (PBS). The medium was Dulbecco modified Eagle's minimum essential medium (Whittaker Bioproducts, U.S.A.) containing 10 V/V % fetal calf serum (FCS, Whittaker Bioproducts, U.S.A.). The above plate was incubated for 3 days at 37° C. and 5% $CO_2$. Then, 25 µl of tetrazolium salt MTT (Sigma, U.S.A.) solution (5 mg/ml) dissolved in PBS was added to each well. After incubation for 4 hours, 0.1 ml of 10% SDS solution dissolved in 0.01N hydrochloric acid was added to each well, and the plate was incubated overnight at 37° C. and 5% $CO_2$. Absorbance at 620 nm was measured using Titertek Multiscan Spectrophotometer (Flow, U.S.A.). The growth inhibitory activity (%) was calculated from the absorbance values in the presence and absence of the compound TAN-1813.

Results:

The compound TAN-1813 inhibited the growth of NIH3T3/K-ras cells by 50% at 0.4 μg/ml.

Experiment 3

In vivo tumor growth inhibitory test

Method:

Cells of human fibrosarcoma strain HT-1080 ($2 \times 10^6$ cells per mouse) were subcutaneously transplanted to nude mice. Three mice were used for each treated group. The compound TAN-1813 (50 mg/kg) was subcutaneously administered to the mice daily for 4 days beginning 10 days after the transplantation. Anti-tumor activity was evaluated by measuring tumor size 18 days after the transplantation of the cancer cells. Average tumor sizes of 3 mice in the untreated (C) and the compound TAN-1813-treated (T) group were measured, to determine the tumor growth inhibitory activity. The tumor size ($mm^3$) was calculated from the formula: $0.5 \times a \times b^2$ by measuring the major axis (mm) (a) and minor axis (mm) (b) with a calibrater.

Results:

The tumor size ratio (T/C$\times$100) was 46 (%). This result shows that the administration of the compound TAN-1813 significantly inhibited the tumor growth.

As shown in the above biological data, the compound TAN-1813 or a salt thereof of the present invention is a novel compound having farnesyltransferase-inhibitory, cell growth inhibitory, and anti-tumor activities.

The compound TAN-1813 or a salt thereof of the present invention has low toxicity, and can be administered to mammals (e.g., rats, mice, cattle, horses, monkeys, humans, etc.) as a farnesyltransferase inhibiting agent comprising it. Thus the compound TAN-1813 or a salt thereof is useful as an active ingredient of a farnesyltransferase inhibiting agent. In addition, the compound TAN-1813 or a salt thereof can be used as an anti-tumor agent to prevent cancer growth and metastasis in mammals. These agents can be prepared by mixing the compound TAN-1813 or a salt thereof with a pharmaceutically acceptable carrier by per se known methods. These agents can be administered parenterally or orally as pharmaceutical compositions.

Examples of pharmaceutical compositions include parenteral compositions such as injections, preparations for drip infusion, external preparations (e.g., preparations for nasal administration, transdermal preparations, etc.), suppositories (e.g., rectal suppositories, vaginal suppositories, etc.), etc.; oral compositions such as capsules, tablets, syrups, powder, granules; or other pharmaceutical compositions.

These compositions can be prepared by per se known methods conventionally used in production of pharmaceutical compositions.

For example, oral compositions can be prepared according to per se known methods by compressing a mixture of the compound TAN-1813 or a salt thereof with pharmaceutically acceptable carriers, e.g., excipients (e.g., lactose, sucrose, starch, etc.), disintegrators (e.g., starch, calcium carbonate, etc.), binders (e.g., starch, gum arabic, carboxymethylcellulose, polyvinylpyrrolidone, hydroxypropylcellulose, etc.), lubricants (e.g., talc, magnesium stearate, polyethylene glycol 6000, etc.), etc. If necessary, the compressed composition is then coated by Der se known methods for the masking of taste, enteric coating, or release prolongation.

Examples of coating agents are hydroxypropylmethylcellulose, ethylcellulose, hydroxymethylcellulose, hydroxypropylcellulose, polyoxyethylene glycol, Tween 80, Brulonick F 68, cellulose acetate phthalate, hydroxypropylmethylcellulose phthalate, hydroxymethylcellulose acetate succinate, Eudragit (manufactured by Rohm, Germany; methacrylic acid-acrylic acid copolymer) and pigments such as titanium oxide and red iron oxide, etc.

When parenteral compositions such as injections can be prepared, a mixture of the compound TAN-1813 or a salt thereof with a dispersing agent [e.g., Tween 80 (manufactured by Atlas Powder, Co., U.S.A.), HCO 60 (manufactured by Nikko Chemicals, Japan), polyethylene glycol, carboxymethyl cellulose, sodium alginate, etc.], preservative (e.g., methylparaben, propylparaben, benzyl alcohol, chlorobutanol, etc.), tonicity agent (e.g., sodium chloride, glycerin, sorbitol, glucose, etc.), etc., is shaped into aqueous injections. Alternatively, the compound or a salt thereof is dissolved, suspended or emulsified in a vegetable oil (e.g., olive oil, sesame oil, peanut oil, cotton seed oil, corn oil, etc.), propylene glycol, etc., to shape it to oily injections.

For example, the compound TAN-1813 or a salt thereof can be shaped into solid, semisolid or liquid topical preparations according to per se known methods. For example, to prepare the above solid preparations, the compound TAN-1813 or a salt thereof as it is, or a mixture thereof with an excipient (e.g., mannitol, starch, fine-crystalline cellulose, etc.), a thickener (e.g., natural rubber, cellulose and derivatives thereof, acrylic acid polymers, etc.), etc., is shaped into powdery compositions. To prepare the above liquid compositions, the compound TAN-1813 or a salt thereof is shaped into oily or aqueous suspensions as in the case of the injections. To prepare semisolid preparations, the compound TAN-1813 or a salt thereof is mixed with an aqueous or an oily gelling agent, or an ointment. Each of these compositions may contain pH-adjusting agents (e.g., carbonic acid, phosphoric acid, citric acid, hydrochloric acid, sodium hydroxide, etc.), preservatives (e.g., parahydroxybenzoates, chlorobutanol, benzalkonium chloride, etc.), etc.

For example, to prepare suppositories, the compound TAN-1813 or a salt thereof can be shaped into oily or water-soluble solid, semisolid or liquid suppositories by per se known methods. Examples of oily bases to be used in the above compositions include glycerides of higher fatty acids (e.g., cacao butter, Wittepsol (manufactured by Dynamite Nobel), etc.), medium aliphatic acids (e.g., Migliol (manufactured by Dynamite Nobel) or vegetable oils (e.g., sesame oil, soybean oil, cotton seed oil, etc.), etc. Examples of water-soluble bases include polyethylene glycols, propylene glycol, etc. Examples of aqueous gel-type vehicles include natural rubbers, cellulose and derivatives thereof, vinyl polymers, acrylic acid polymers, etc.

These compositions can be administered orally or parenterally. For example, when they are orally administered to humans, the dose varies with the kind of subject disease, severity of the disease, patient's age, etc. However, the daily dose of the compound TAN-1813 or a salt thereof for treating diseases is normally about 1 to about 40 mg, preferably about 2 to about 30 mg, per adult (body weight: 50 kg). These compositions can be administered once or in two to three divided portions daily. For example, when the compound TAN-1813 or a salt thereof is parenterally administered in the form of injections, e.g., subcutaneously, intravenously or intramuscularly, the daily dose is about 0.5 to about 30 mg, preferably about 1 to about 20 mg, per adult (body weight: 50 kg).

As described above, the present invention provides the compound TAN-1813 or a salt thereof having potent farnesyltransferase-inhibitory, cell growth inhibitory and anti-tumor activities, its production, and a farnesyltransferase inhibiting agent comprising the compound TAN-1813 or a salt thereof.

The compound TAN-1813 or a salt thereof is of low toxicity, and is useful as a farnesyltransferase inhibiting agent. In addition, the compound TAN-1813 or a salt thereof has anti-tumor activity, in particular, activity to prevent growth and metastasis of tumor harboring the ras gene mutation, and therefore is also useful as an anti-tumor agent.

The following Examples and Preparations further illustrate the present invention in detail but are not to be construed to limit the scope of the invention. All the percent (%) indicating the compositions of the media are weight/volume percent unless otherwise indicated. The mixing ratios of solvents are ratios by volume unless otherwise indicated.

Symbols used in the example are of the following meaning.

s: singlet, d: doublet, t: triplet, q: quartet, dd: double doublet, ddd: double double doublet, m: multiplet, br: broad, J: coupling constant.

EXAMPLE 1

Preparation of the compound (I): 5-[2,5-dihydro-4-(1-octen-3-yl)-2,5-dioxo-1H-pyrrole-3-carbonyl]-8a-hydroxy-4,6-dimethyl-1,2,3,4,4a,5,6,8a-octahydro-2-naphthalenecarboxylic acid Phoma sp. strain FL-41510 (FERMBP-4632) cultivated at 28° C. for 7 days on a slant medium containing 2.4% potato dextrose broth (manufactured by Difco, U.S.A.), 2% agar in water was inoculated in a seed culture (500 ml in a 2 L Sakaguchi flask, pH 6.0) containing 2% glucose, 3% maltose, 1.5% raw soybean flour, 1% corn steep liquor, 0.5% peptone, 0.3% yeast extract, 0.3% sodium chloride and 0.05% Actocol (an antifoaming agent manufactured by Takeda Chemical Industries, Ltd., Japan). Reciprocating shaking culture was carried out at 24° C. for 48 hours. The resulting culture broth (1 l) was transferred to a 50-liter fermentor containing the above seed culture (30 l), and subjected to aerobic agitating culture (aeration rate, 30 l/min; agitation, 280 rpm) at 24° C. for 48 hours to obtain a seed culture broth. The seed culture broth (6 l) was inoculated in a 200 l fermentor containing a main culture medium (120 l, pH 7.5) consisting of 1% glucose, 4% dextrin, 0.5% raw soybean flour, 0.5% malt extract, 0.5% peptone, 0.2% yeast extract, 0.05% ferrous sulfate heptahydrate, 0.05% magnesium sulfate heptahydrate, 0.05% manganese sulfate tetrahydrate, 0.1% potassium dihydrogen phosphate, 0.5% calcium carbonate and 0.05% Actocol, and subjected to aerobic agitating culture (aeration rate, 120 l/min; agitation, 150 rpm) at 24° C. for 114 hours to obtain a culture broth.

The culture broth (105 l) thus obtained was adjusted to pH 2.6 and ethyl acetate (100 l) was added, and the mixture was stirred for 30 minutes. After adding Radiolite 600 (manufactured by Showa Kagaku Kogyo, Japan) to the mixture, the mixture was filtered. The resulting organic layer (80 l) was washed with water (30 l) twice, and concentrated to give a crude oil (78 g). This oil was dissolved in a small amount of a mixture of chloroform and ethyl acetate, and subjected to column chromatography on silica gel (1.3 l, Silica gel 60, 70–230 mesh, E. Merck, Germany). The column was washed successively with hexane (2 l), hexane-acetone (9:1)(2 l) and hexane-acetone (8:2)(5 l), and then the active compound was eluted with hexane-acetone (6:4) (2 l). The eluate was concentrated to give a brown powder (8.9 g). This powder was divided into 5 equal parts. Each of them was subjected to high performance liquid chromatography (HPLC) (column: YMC-Pack S-363-15, I-15, ODS, manufactured by YMC, Japan; solvent: 58% acetonitrile-10 mM phosphate buffer (pH 3.0); flow rate: 20 ml/min) to obtain fractions each of which contains 20 ml of the eluate. In each eluting operation, the fraction Nos. 22 to 32 were combined (total volume, 1.1 l), concentrated to a final volume of 400 ml, adjusted to pH 3.0, and extracted with ethyl acetate (2×200 ml). The ethyl acetate layers were combined, washed with water (2×150 ml), dried over anhydrous sodium sulfate, and concentrated. The resulting residue was dissolved in a small amount of ether. Addition of hexane gave the compound TAN-1813 as a pale yellow powder (2.1 g).

The physical and chemical properties of the compound TAN-1813 thus obtained are as follows.

(1) Appearance: Pale yellow powder (2) Mass spectroscopy (EI-MS): m/z 457 $(M)^+$ (3) Molecular formula: $C_{26}H_{35}NO_6$ (4) Elemental analysis (%):
Calcd. for $C_{26}H_{35}NO_6$: C, 68.25; H, 7.71; N, 3.06
Found: C, 67.95; H, 7.63; N, 2.93

Figure 1:
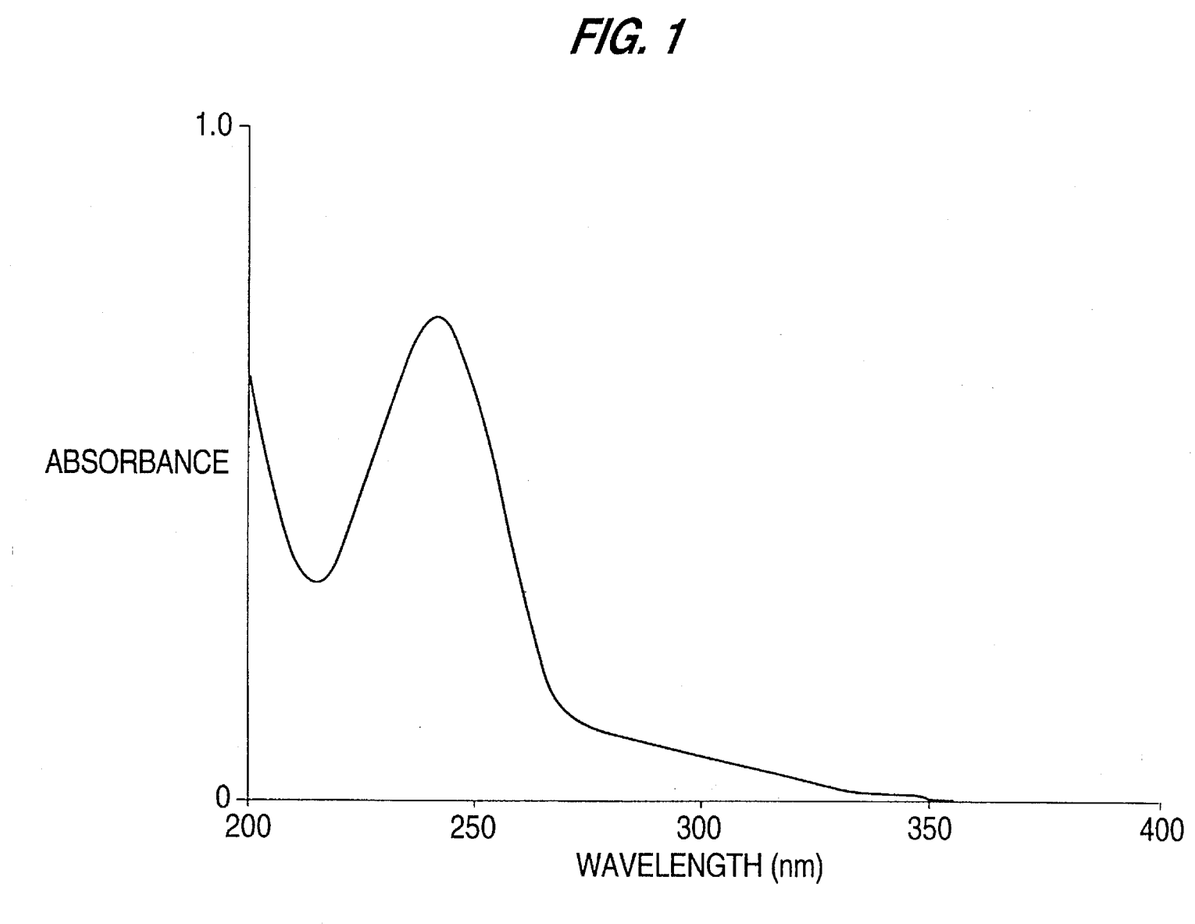
FIG. 1 shows an ultraviolet (UV) absorption spectrum (in methanol) of the compound TAN-1813.

(5) Ultraviolet (UV) absorption spectrum: in methanol (FIG. 1), Max.: 240 nm ($\epsilon$16500)

Figure 2:
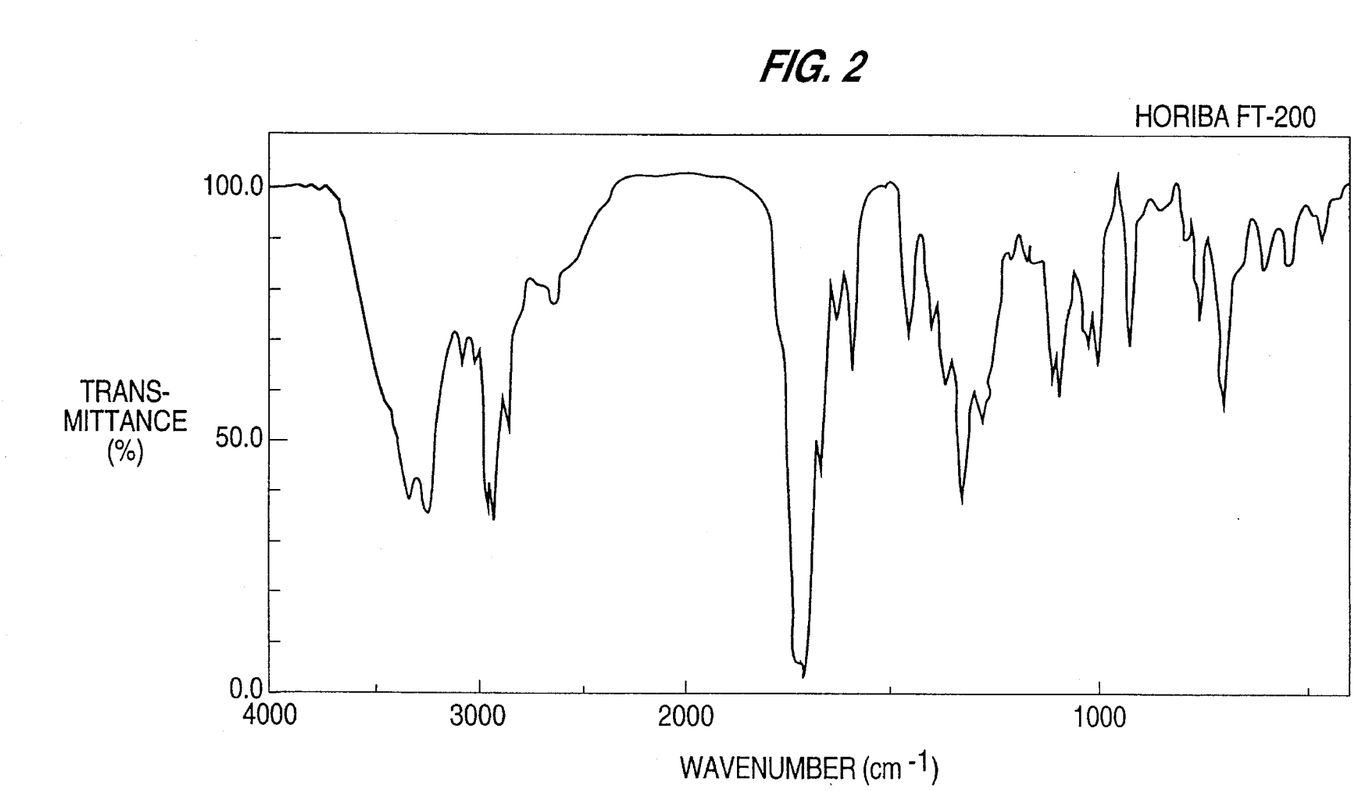
FIG. 2 shows an infrared (IR) absorption spectrum (in KBr pellet) of the compound TAN-1813.

(6) Infrared absorption spectrum: in KBr pellet, main frequencies are as follows $(cm^{-1})$ (FIG. 2): 3330, 3250, 2965, 2935, 2860, 2630, 1725, 1710, 1670, 1595, 1460, 1335, 1095, 1005, 925, 760, 700.

Figures 3A, 3B:
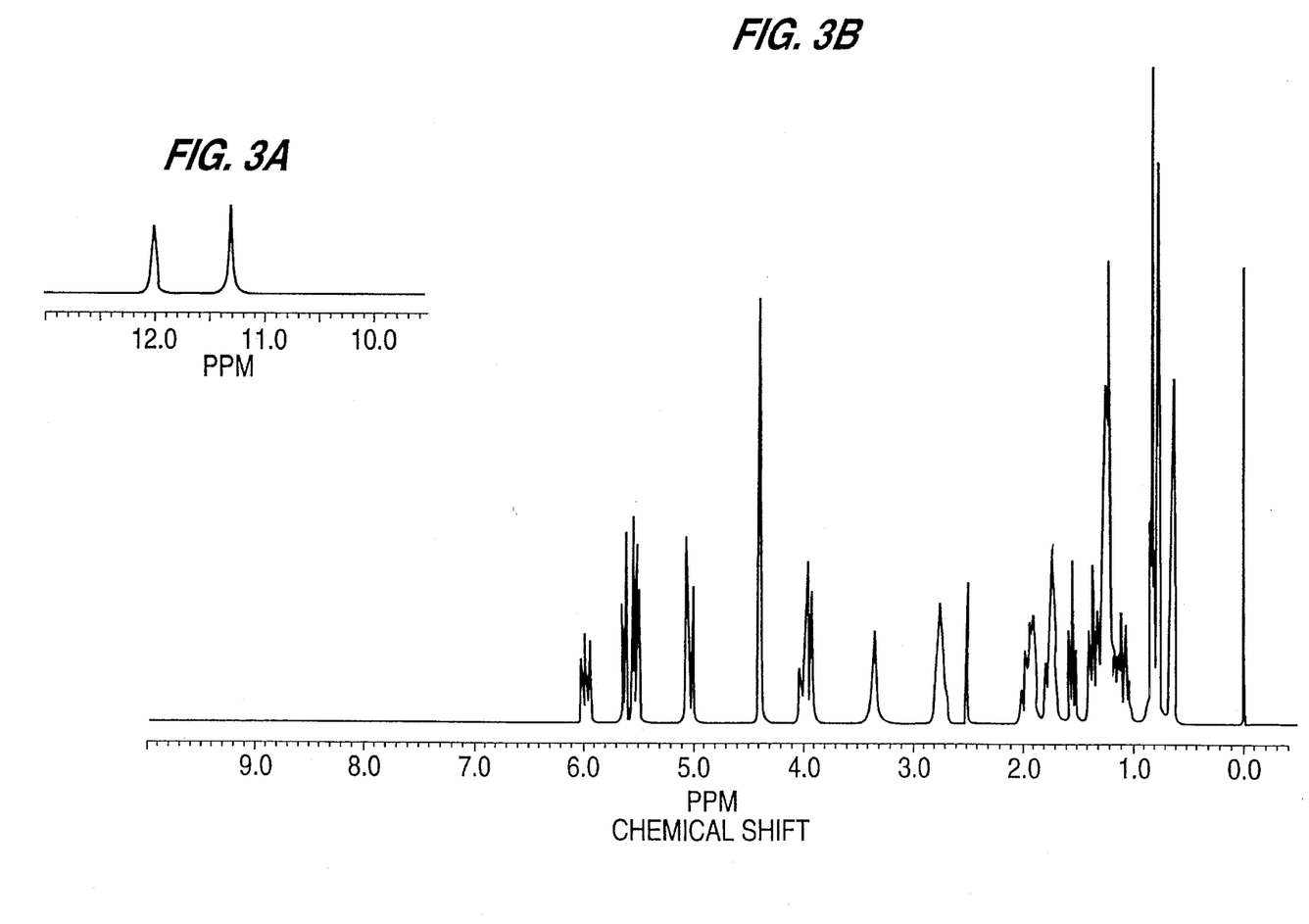
FIG. 3 shows a $^1$H-nuclear magnetic resonance (NMR) spectrum (in $(CD_3)_2SO$, tetramethylsilane being added as an internal standard) of the compound TAN-1813.

(7) $^1$H-Nuclear magnetic resonance (NMR) spectrum: 300 MHz, in $(CD_3)_2SO$ (tetramethylsilane was used as an internal standard (0 ppm)) (FIG. 3).

δ ppm: 0.64(3H,d,J=6.7 Hz), 0.77(3H,d,J=7.4 Hz), 0.83(3H,t,J=6.6 Hz), 1.09(1H,m), 1.15(1H,m), 1.24(4H,m), 1.30(1H,m), 1.36(1H,t,J=12.8 Hz), 1.55(1H,t,J=10.5 Hz), 1.71(2H,m), 1.77(1H,m), 1.92(2H,m), 2.74(1H,m), 2.77(1H,m), 3.94(1H,dd,J=10.5,7.8 Hz), 4.00(1H,q,J=8.3 Hz), 4.41(1H,s), 5.05(1H,brd,J=10.2 Hz), 5.07(1H,brd,J=17.1 Hz), 5.54(1H,dd,J=9.5,3.7 Hz), 5.65(1H,dd,J=9.5,2.1 Hz), 5.99(1H,ddd,J=17.1,10.2,8.3 Hz), 11.29(1H,brs), 11.99(1H,brs).

Figure 4:
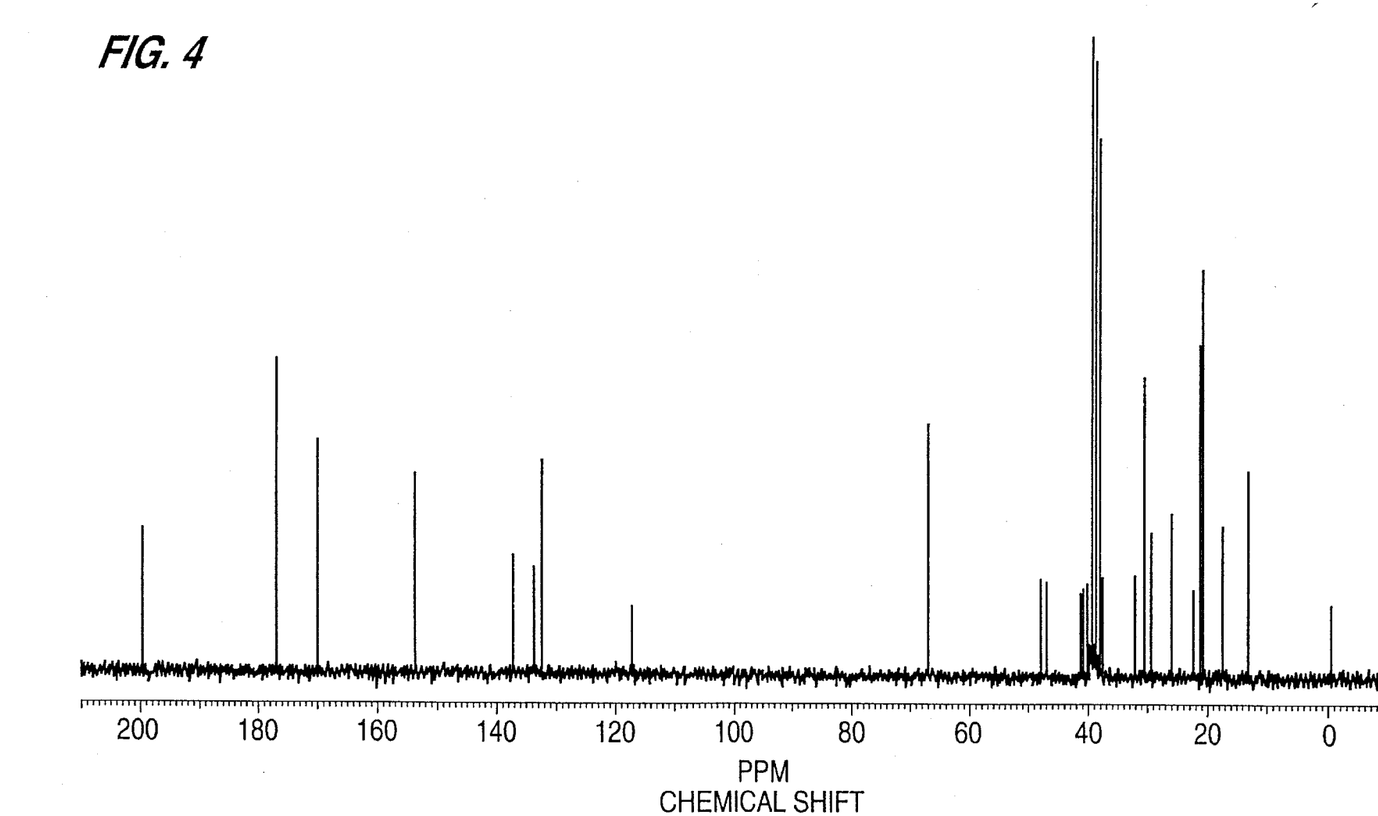
FIG. 4 shows a $^{13}$C-nuclear magnetic resonance (NMR) spectrum (in $(CD_3)_2SO$, tetramethylsilane being added as an internal standard) of the compound TAN-1813.

(8) $^{13}$C-Nuclear magnetic resonance spectrum: 75 MHz, in $(CD_3)_2SO$ (tetramethylsilane was used as an internal standard (0 ppm)) (FIG. 4):

δ ppm: 13.7($CH_3$), 17.6($CH_3$), 21.9($CH_2$), 23.2($CH_3$), 26.6($CH_2$), 29.8(CH), 30.7($CH_2$), 31.2(CH), 32.2($CH_2$), 37.7(CH), 38.3($CH_2$), 41.0(CH), 41.3($CH_2$), 47.2(CH), 48.2(CH), 67.1(Q), 117.4($CH_2$), 132.9(CH), 133.1(Q), 134.1(CH), 137.3(CH), 153.4(Q), 169.9(Q), 170.2(Q), 176.8(Q), 199.6(Q). In this data, Q is a quaternary carbon atom, CH is a methine carbon atom, $CH_2$ is a methylene carbon atom, and $CH_3$ is a methyl carbon atom.

(9) Specific rotation: $[\alpha]_D^{22}$: −48.9° (c=0.52, methanol).

(10) High performance liquid chromatography (HPLC): Column: YMC-Pack A-312 ODS (manufactured by YMC, Japan) Mobile phase: 65% acetonitrile-10 mM phosphate buffer (pH 3.0)

Flow rate: 2.0 ml/min

Detection: UV absorption, 214 nm, 254 nm

Retention time: 4.5 min (11) Thin layer chromatography (TLC): A: Support: Silica gel 60 F254 TLC plate (manufactured by E. Merck, Germany)

Eluent: Chloroform-methanol (9:1)

Rf: 0.43 B: Support: Silica gel 60 F 254 TLC plate (manufactured by E. Merck, Germany)

Eluent: Hexane-acetone (1:1)

Rf: 0.50

(12) Color reaction:

Positive: Phosphomolybdic acid, iodine, conc. sulfuric acid, potassium permanganate Negative: Ninhydrin, Ehrlich reagent, Barton reagent (13) Acidity: Acidic (14) Solubility:

Readily soluble in methanol, ethyl acetate, chloroform, and dimethyl sulfoxide

Slightly soluble in water, and hexane

Based on the above data, the following chemical structure of the compound TAN-1813 was determined.

Preparation 1

All of the ingredients described below were mixed with the compound TAN-1813 obtained in Example 1, and the mixture was filled into gelatin capsules to prepare capsules containing the compound TAN-1813 (30 mg per capsule).

| Compound TAN-1813 | 30 mg |
| --- | --- |
| Lactose | 100 mg |
| Corn starch | 40 mg |
| Magnesium stearate | 10 mg |
| Total | 180 mg |

Preparation 2

A mixture of the compound TAN-1813 obtained in Example 1 and magnesium stearate was granulated using an aqueous solution of soluble starch, dried, and mixed with lactose and corn starch. The resulting mixture was compressed to obtain tablets having the following formulation.

| Compound TAN-1813 | 30 mg |
| --- | --- |
| Lactose | 65 mg |
| Corn starch | 30 mg |
| Soluble starch | 35 mg |
| Magnesium stearate | 20 mg |
| Total | 180 mg |

Preparation 3

All of the ingredients described below were mixed with the compound TAN-1813 obtained in Example 1, and the mixture was filled into gelatin capsules to prepare capsules containing the compound TAN-1813 (30 mg per capsule).

| Compound TAN-1813 | 10 mg |
| --- | --- |
| Lactose | 110 mg |
| Corn starch | 50 mg |
| Magnesium stearate | 10 mg |
| Total | 180 mg |

Preparation 4

10 mg each of the compound TAN-1813 was distributed into vials to prepare a composition for intravenous injection. Mannitol (50 g) was dissolved in distilled water for injection (1 liter) containing polyethylene glycol 400 (30% W/W). The solution was subjected to filtration under sterilization, and 1 ml each of which was then charged into vials to prepare a composition for solubilizer. The above compositions were assembled and used as a kit.

What is claimed is:

1. A compound of the formula (I):

or a pharmaceutically acceptable salt thereof.

2. A method of inhibiting farnesyltransferase comprising treating a patient in need thereof units a farnesyltransferase inhibiting amount of a compound of claim 1 or a pharmaceutically acceptable salt thereof.

3. An anti-tumor agent comprising about 1 to about 40 mg daily dose, per 50 kg body weight, of a compound of claim 1 or a pharmaceutically acceptable salt thereof.

4. A pharmaceutical composition comprising a compound of claim 1 or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 5,498,627
DATED : March 12, 1996
INVENTOR(S) : Takafumi ISHII et al.

It is certified that error appears in the above-identified patent and that said Letters Patent is hereby corrected as shown below:

Front page, right column, line 3: change "Zenopus" to --Xenopus--.

Front page, right column, line 15: change "farneslyltransferases" to --farnesyltransferases--.

Front page, right column, line 23: delete "35 U.S.C.".

Column 1, line 19: change "Proteins" to --proteins--.

Column 2, line 42: change "TN-1813" to --TAN-1813--.

Column 8, line 3: change "Der" to --per--.

Column 10, line 24: after "Infrared" insert --(IR)--.

Column 12, claim 2, line 2: change "units" to --with--.

Signed and Sealed this

Twenty-third Day of December, 1997

Attest:

BRUCE LEHMAN

Attesting Officer

Commissioner of Patents and Trademarks